US011733164B2

(12) United States Patent
Löbbert

(10) Patent No.: US 11,733,164 B2
(45) Date of Patent: Aug. 22, 2023

(54) OPTICAL MEASUREMENT PROBE

(71) Applicant: Endress+Hauser Conducta GmbH+Co. KG, Gerlingen (DE)

(72) Inventor: Andreas Löbbert, Waldheim (DE)

(73) Assignee: Endress+Hauser Conducta GmbH+Co. KG, Gerlingen (DE)

(*) Notice: Subject to any disclaimer, the term of this patent is extended or adjusted under 35 U.S.C. 154(b) by 355 days.

(21) Appl. No.: 16/107,905

(22) Filed: Aug. 21, 2018

(65) Prior Publication Data

US 2019/0064065 A1 Feb. 28, 2019

(30) Foreign Application Priority Data

Aug. 22, 2017 (DE) .................... 10 2017 119 171.2

(51) Int. Cl.
*G01N 21/85* (2006.01)
*G01N 21/64* (2006.01)
(Continued)

(52) U.S. Cl.
CPC ............ *G01N 21/643* (2013.01); *C12Q 1/06* (2013.01); *G01N 21/645* (2013.01); *G01N 21/6428* (2013.01); *G01N 21/7703* (2013.01); *G01N 21/80* (2013.01); *G01N 21/82* (2013.01); *A61B 5/1455* (2013.01); *G01N 21/8507* (2013.01);
(Continued)

(58) Field of Classification Search
None
See application file for complete search history.

(56) References Cited

U.S. PATENT DOCUMENTS 4,269,516 A     5/1981  Lübbers et al.
4,577,110 A  *  3/1986  MacBride ............ G01N 21/645
                                                    250/461.2
(Continued)

FOREIGN PATENT DOCUMENTS

CN     1147301 A      4/1997
CN     1507560 A      6/2004
CN   101209201 B     12/2011

OTHER PUBLICATIONS

Search Report for German Patent Application No. 10 2017 119 171.2, German Patent Office, dated May 5, 2018, 7 pp.
(Continued)

*Primary Examiner* — Neil N Turk
(74) *Attorney, Agent, or Firm* — Christopher R. Powers; Endress+Hauser (USA) Holding, Inc.

(57) ABSTRACT

The present disclosure relates to an optical measurement probe for the detection of measurement values correlating with a measurand of a measuring medium, including a probe housing having at least one immersion region structured to be immersed in the measuring medium, a radiation source arranged in the probe housing, a radiation receiver arranged in the probe housing, and an indicator chamber formed in the probe housing and sealed via a membrane arranged in the immersion region of the probe housing, wherein an indicator is contained in the indicator chamber, the indicator including an AIE-active substance dissolved in an indicator solution or in an indicator gel, which AIE-active substance is a substance formed from species, molecules, complexes or clusters whose luminescence efficiency is increased via formation of aggregates containing the species.

22 Claims, 4 Drawing Sheets

(51) Int. Cl.
*G01N 21/77* (2006.01)
*C12Q 1/06* (2006.01)
*G01N 21/80* (2006.01)
*G01N 21/82* (2006.01)
*A61B 5/1455* (2006.01)

(52) U.S. Cl.
CPC ........... *G01N 2021/6434* (2013.01); *G01N 2021/6439* (2013.01); *G01N 2021/775* (2013.01); *G01N 2021/7733* (2013.01); *G01N 2021/7786* (2013.01); *G01N 2021/825* (2013.01)

(56) References Cited

U.S. PATENT DOCUMENTS

| | | |
|---|---|---|
| 6,285,807 B1 | 9/2001 | Walt et al. |
| 8,134,017 B1 | 3/2012 | Kamino et al. |
| 9,051,598 B2 * | 6/2015 | Tang ............ C12Q 1/54 |
| 2005/0063869 A1 * | 3/2005 | Follonier ......... G01N 33/54373 422/82.05 |
| 2009/0075321 A1 * | 3/2009 | Obeid ............... A61B 5/6848 435/29 |
| 2013/0092846 A1 * | 4/2013 | Henning ........... G01N 21/6408 250/564 |
| 2013/0164531 A1 | 6/2013 | Natarajan et al. |
| 2015/0192589 A1 | 7/2015 | Gao et al. |
| 2016/0211470 A1 | 7/2016 | Tang et al. |
| 2016/0349245 A1 | 12/2016 | Zhang et al. |
| 2017/0168037 A1 | 6/2017 | Moore et al. |
| 2017/0168041 A1 | 6/2017 | Liu et al. |

OTHER PUBLICATIONS

Chuanlong Maio, et al., Reprint of "AIE luminogen functionalized mesoporous silica nanparticles as efficient flourescent sensor for explosives detection in water", Microporous and Mesoporous Materials, Apr. 2014, 6 pp.

Zajko, Spela, et al., The Effects of Different Sterilization Procedures on the Optical Polymer Oxygen Sensors, Sensors and Actuators, B 177(2013), pp. 86-93.

* cited by examiner

OPTICAL MEASUREMENT PROBE

CROSS-REFERENCE TO RELATED APPLICATION

The present application is related to and claims the priority benefit of German Patent Application No. 10 2017 119 171.2, filed on Aug. 22, 2017, the entire contents of which are incorporated herein by reference.

TECHNICAL FIELD

The invention relates to an optical measurement probe for the detection of measurement values correlating with a measurand of a measuring medium.

BACKGROUND

Optical measurement probes may be used as a component of an inline sensor in process metrology or analysis engineering. Sensors that comprise a measurement probe integrated into a process vessel (for example, a reactor or a tube) to monitor a measurand of a process performed in the process vessel are referred to as inline sensors. An inline sensor thus directly detects the measurand in the process to be monitored or controlled, for example, in a measuring fluid that is used in the process. With inline sensors, no extraction and pre-treatment of a sample from the process is, therefore, necessary for determining a measurand. To integrate the measurement probe into the process vessel, this may, for example, be fixed in a wall of the process vessel by means of an adapter or a fitting. In addition to the measurement probe, an inline sensor may comprise an electronic evaluation device connected to the measurement probe, and possibly built into the sensor. The sensor is commonly arranged outside of the process vessel.

Among other things, optical or optochemical sensors may be used to determine the concentration of gaseous or dissolved analytes in a measuring fluid, e.g., in a measuring gas or in a measuring liquid, or of other measurands that are related to the concentration of the analytes in the measuring fluid, for example, an activity or a partial pressure. Such sensors may include a sensor element that is often integrated into a measurement probe, which sensor element is brought into contact with the measuring fluid for measurement of the measurand, and whose optical properties change as a function of the measurand. For example, the sensor element may have a membrane in which is contained an indicator that may be excited to emit luminescence radiation. For example, the indicator may be a fluorophore whose fluorescence radiation may be extinguished in the presence of the analyte due to interaction with it. This effect is also referred to as fluorescence extinguishing or fluorescence quenching. Optical sensors based upon the effect of fluorescence extinguishing include a sensor circuit (in certain cases, being electronic) that is designed to detect, on the basis of fluorescence measurements, e.g., using time-correlated individual photon counting (fluorescence intensity and decay time), using an idle time of the fluorescence detection (technical term: gated detection), using phase modulation, and/or with regard to a second wavelength (dual wavelength rationing), measurement values of the analyte concentration or a measurand correlated with the analyte concentration. For example, such optochemical sensors may be used to determine concentrations of analytes such as oxygen or other molecules, but also to measure the pH value or concentrations of specific ionic analytes in a measuring fluid.

However, such optical sensors, such as those that serve to measure pH value and/or an ion concentration, also have disadvantages. For example, such optical sensors often exhibit a slow response characteristic. For example, the chemical stability of sensors whose sensor element includes an indicator contained in a polymer membrane is often ensured only within a relatively limited temperature range. For example, in these instances, sterilizations at temperatures above 120° C. may lead to damage of the sensor element, or at least to an alteration of properties that are relevant to the measurement. With optochemical sensors, in the course of their service life, a drift of the measurement signal (also referred to as sensor drift) is often observed that is caused by a bleaching and/or leaching of the indicator from the sensor element. This drift makes frequent servicing necessary, for example, a frequent calibration of the sensors or a regular exchange of the sensor element, or at least of the membrane containing the indicator. The production of such optochemical sensors may also be costly, in particular, if it is sought to preserve the sensor element, via the most varied protective measures known in the prior art, against premature bleaching or leaching of the indicator.

Optochemical oxygen sensors in which the indicator is immobilized in an oxygen-permeable polymer matrix constitute an exception. This sensor type does not have the aforementioned problems and has found a wide acceptance in recent years. One cause of the lesser stability of many optochemical ion sensors and pH sensors in comparison to such oxygen sensors is that the fluorophores used as an indicator in said ion sensors and pH sensors are hydrolysis-sensitive and photosensitive due to their polarity, and, in contact with solvents, an accelerated material transport of decomposition products may occur. In particular, with an aqueous measuring fluid, dyes that are initially immobilized in the membrane may easily be flushed out again. This causes a degradation of the indicator and a quick and continuous decrease in the indicator concentration in the membrane. This, on the one hand, limits the service life of the sensor element. On the other hand, the continuous decrease in the indicator concentration is accompanied by a significant sensor drift, such that a frequent calibration or adjustment is necessary to ensure sufficiently reliable measurement values with these sensors.

It would be desirable to provide optical inline sensors that are less costly in terms of production and servicing than the aforementioned optical sensors. In particular, these sensors should be operable maintenance-free and without sensor drift over a longer time period.

In recent years, the effect of aggregation-induced emission (AIE) has become known. This effect may be observed on specific substances—what are known as AIE-active substances—whose luminescence efficiency increases with aggregation of the molecules of this substance. With constant, lasting concentration of the AIE-active substances, in the case of an aggregate formation, an increase in their emission intensity is thus to be observed. The intensity increase or luminescence efficiency increase is generally proportional to the concentration change of analytes causing or influencing an aggregation with participation of molecules of the AIE-active sub stance.

Presently, there are many activities for exploiting the AIE for the detection of analytes, but most are still in the academic research stage. In U.S. Pat. No. 9,051,598 B2, a detection method for glucose in an aqueous sample is described in which (1,2-diphenylethene-1,2-diyl)bis(1,4-phenylene)-1,1'-diboric acid (TPEDB) serves as an AIE-active substance. To detect glucose, the TPEDB dissolved in an alkaline dimethyl sulfoxide solution is added to the sample, and the increase in fluorescence intensity that thereby occurs is detected.

In order to monitor a process engineering and/or biotechnological process with this method, it would be necessary to extract samples of the measuring fluid from the process, which samples would then need to be mixed with the detection reagent comprising the AIE-active substance in order to detect the analyte content of the sample using a fluorescence measurement. The sampling requires an equipment expenditure and includes the risk of unwanted substances from the environment penetrating into the process; on the other hand, a measurement result determined from an extracted sample in the laboratory is available only with a time delay that is significant under the circumstances. A control or regulation of the process using the measurement results of a laboratory method is therefore often impossible, or at least problematic. In order to be able to provide the measurement results as promptly as possible, largely avoiding the cited disadvantages of the sampling, an inline sensor would therefore be desirable that determines the analyte concentration, or a measurand correlated with the analyte concentration, directly in the process, without influencing said process. The laboratory method described in U.S. Pat. No. 9,051,598 B2 is not suitable for this.

SUMMARY

The present disclosure discloses a measurement probe for determining a measurand for an optical inline sensor, e.g., an analyte concentration in a measuring fluid or a measurand dependent upon the analyte concentration, which measurement probe is low-maintenance. In particular, the measurement signal of the measurement probe of the present disclosure has a lower drift compared to conventional optical inline sensors, and, accordingly, is reliably operable over a longer time period without a calibration/adjustment or other maintenance measure.

According to the present disclosure, this aim is achieved by an optical measurement probe unit having the features of claim 1. Advantageous embodiments are listed in the dependent claims.

The optical measurement probe according to the present disclosure for the detection of measurement values of a measurand of a measuring fluid comprises a probe housing which has an immersion region designed to be immersed in the measuring fluid; a radiation source arranged in the probe housing; a radiation receiver arranged in the probe housing; and an indicator chamber formed in the probe housing, which indicator chamber is sealed via a membrane arranged in the immersion region of the probe housing, wherein an indicator is contained in the indicator chamber, which indicator comprises an AIE-active substance dissolved in an indicator solution or in an indicator gel, which AIE-active substance is a substance which is formed from species, molecules, complexes or clusters and whose luminescence efficiency is increased via formation of aggregates containing the species.

The measurement probe according to the present disclosure may be used as an inline sensor, wherein the membrane prevents the AIE-active substance enclosed in the indicator chamber from exiting into the measuring fluid. The probe housing allows the integration of the measurement probe into a wall of a container containing the measuring fluid, e.g., a wall of a reactor or of a tube, by means of an adapter. As opposed to the method described in U.S. Pat. No. 9,051,598 B2, a sample extraction and pre-treatment is thus not required to determine the measurand.

The AIE-active substances may be moderately soluble in aqueous solutions. By sealing a measurement region against a measuring fluid using a membrane, the AIE concentration is essentially held constant and protected from washing out. Those functional groups of species of AIE-active substances that play a role in aggregate formation may be polar in nature. These functional groups are chemically stable and thereby are less sensitive, or even entirely insensitive, with regard to aging processes, such as those that are triggered by hydrolysis. The measurement probe according to the present disclosure may accordingly be operated over longer periods of time than the conventional measurement probes, without adjustment or calibration or other maintenance measures.

Species of the AIE-active substance may, for example, be molecules, ions, coordination compounds, e.g., complexes, or clusters. Aggregates containing the species of the AIE-active substance may be self-aggregates, i.e., those aggregates that consist exclusively of the species of the AIE-active substance, or aggregates comprising additional chemical species, e.g., complexes or clusters, in addition to the species of the AIE-active substance.

In an embodiment, the measurand may represent a concentration of an analyte in the measuring medium. In such an embodiment, the membrane is permeable to the analyte, such that the analyte may penetrate into the indicator chamber and interact there with the AIE-active species. For example, the analyte may influence (i.e., cause or promote or even interfere with) a formation of aggregates containing the species of the AIE-active substance.

One possibility of influencing the aggregate formation via an analyte is that the species of the AIE-active substance enter into a self-aggregation, thus forming aggregates that are formed only from the species of the AIE-active substance, wherein the analyte interferes with the self-aggregation of the AIE-active species. In such instances, a reduction in the luminescence efficiency of the indicator or of the AIE-active substance is observable in the presence of the analyte. In another example, the species of the AIE-active substance may enter into a self-aggregation promoted by the presence of the analyte or may form aggregates with the analyte. In this instance, the presence of the analyte leads to an increase in the luminescence efficiency of the indicator or of the AIE-active substance. In all instances, the influencing of the aggregate formation by the analyte alters the luminescence intensity of the AIE-active substance. Accordingly, in the first example, the intensity decrease in the luminescence radiation received by the radiation receiver, which decrease is to be detected in case of a consistent concentration of the AIE-active substance in the indicator, and, in the second example, the corresponding intensity increase in the luminescence radiation received by the radiation receiver, which increase is to be detected in case of a consistent concentration of the AIE-active substance in the indicator, are a measure of the concentration of the analyte in the measuring fluid.

In another embodiment, the measurand may be a variable other than an analyte concentration, e.g., a temperature or a pressure that influences the formation of aggregates containing the species of the AIE-active substance, e.g., a self-aggregation. In this instance, the change of the measurand may promote or interfere with the formation of aggregates that comprise the species of the AIE-active substance. Accordingly, an intensity change in the luminescence radiation that can be detected using the radiation receiver is a measure of the measurand.

The indicator may comprise an indicator solution or an indicator gel in which the AIE-active substance is dissolved. If applicable, the indicator may comprise additional components that, for example, serve to set a specific pH value of the indicator and/or to influence the solubility of the AIE-active substance in the indicator solution or the indicator gel. In this embodiment, the membrane is advantageously impermeable to the indicator, or at least to components of the indicator e.g., to the molecules of the AIE-active substance. In this way, the concentration of the AIE-active substance may be held constant over long periods of time, and thus a sensor drift may be avoided.

As solvents or as auxiliary substances that influence, e.g., improve, the solubility of the AIE-active substance, higher-molecular substances may be considered. For example, dimethyl sulfoxide (DMSO) may be considered as a solvent or as an auxiliary substance for poorly water-soluble AIE-active substances, e.g., TPE (tetraphenyl ethylene) or TPE derivatives, but higher-molecular compounds are preferred. What is understood here by a higher-molecular compound is a compound having a molecular weight of more than 100 g/mol, more than 200 g/mol, more preferably, more than 500 g/mol, more than 1,000 g/mol, or even more than 10,000 g/mol. In addition to their effect in improving the solubility of the AIE-active substance, these have the additional advantage that, due to their molecular size, they cannot escape through the membrane into the measuring fluid, even if the membrane has pores or micro-holes so as to be permeable to an analyte. Examples of suitable solvents or auxiliary substances are oligomers, polymers or dendrimers with units of dimethyl sulfoxide, methylvinyl sulfone, allylmethyl sulfone, ethylvinyl sulfone, or polyethylene sulfone, or combinations of these.

In a further embodiment, the indicator chamber may be arranged in a sensor capsule connected to a probe body to form the probe housing, such as a sensor capsule that can be exchanged. This allows the sensor capsule to be exchanged for a new sensor capsule after consuming the indicator, e.g., in the event of a concentration decrease in the AIE-active substance below a concentration limit value due to the AIE-active substance washing out, or chemical or photochemical degradation of the AIE-active substance. In this way, parts of the measurement probe that are accommodated in the probe housing and that are exposed to less wear, e.g., a luminescence measurement device comprising the radiation source, the radiation receiver, and a sensor circuit, may be retained, whereas the shorter-lived sensor capsule may be regularly exchanged.

The indicator chamber and/or—in the event that the measurement probe possesses a sensor capsule comprising the indicator chamber—the sensor capsule may additionally be provided with tempering agents or coolants, e.g., an active fluid tempering unit or Peltier tempering unit, and/or with passive cooling elements, for example, cooling fins. The measurement probe may additionally comprise one or more sensors that monitor the composition of the indicator contained in the indicator chamber.

The radiation source, the radiation receiver, and a sensor circuit electrically connected to the radiation source and the radiation receiver may be arranged in the probe body. The sensor circuit is designed to detect and possibly evaluate detector signals of the radiation receiver. The sensor circuit may be designed to output the detector signals of the radiation receiver, or signals derived therefrom, as measurement signals to a superordinate unit, for example, an operator device, a measuring transducer, or a controller. For example, the sensor circuit may comprise a microprocessor and a memory, wherein an operating program is stored in the memory, which operating program may direct the microprocessor to operate the light source, the radiation receiver, and the sensor circuit, so as to determine measurement values of the measurand based upon luminescence measurements. The detection of luminescence measurement values may take place in a known manner.

The measurement probe may comprise means for radiating radiation emitted by the radiation source into the indicator chamber, e.g., using an optical waveguide for guiding radiation emitted by the radiation source into the indicator chamber, and means for radiating luminescence radiation from the indicator chamber onto the radiation receiver, e.g., using an optical waveguide for guiding luminescence radiation from the indicator chamber onto the radiation receiver.

The indicator chamber may be fluidically connected via a first fluid conduit to at least one reservoir arranged outside of the indicator chamber, which reservoir contains the indicator, for example, the aforementioned indicator solution. The indicator chamber may be fluidically connected to a second fluid conduit for liquid discharge. The second fluid conduit may be connected to a collection container to capture consumed indicator. In this embodiment, the indicator present in the indicator chamber may be exchanged with indicator from the reservoir at regular intervals, as needed, or continuously. For this, the measurement probe may comprise means for transporting fluid from the reservoir into the indicator chamber, and for transporting fluid from the indicator chamber into the second fluid conduit. Such means may comprise valves, pumps, sloping fluid conduits, or other means for generating pressure gradients along which fluid can be transported. The at least one reservoir and/or the collection container may be arranged inside the probe housing. Alternatively, the reservoir and/or the collection container may be arranged outside of the probe housing. In this instance, the first and/or second fluid conduits are directed out of the probe housing to fluidically connect the reservoir and/or the collection container to the indicator chamber.

The indicator chamber may advantageously be fluidically connected to multiple, e.g., two or three, reservoirs arranged outside of the indicator chamber. Each of the reservoirs may comprise an indicator that differs from the indicators present in the additional reservoir. For example, a first indicator that is suitable for determining the concentration of a first analyte may be contained in a first reservoir, whereas a second indicator that is suitable for determining the concentration of a second analyte different from the first analyte is contained in a second reservoir. During operation of the measurement probe, it is then possible to selectively introduce the first or the second indicator into the indicator chamber, depending upon the selection or in alternation, to determine the concentration of the first or the second analyte. In this instance, the membrane is designed so that both the first and the second analytes pass into the indicator chamber through the membrane. In this embodiment, the indicator chamber is additionally connected to at least one collection container for capturing consumed indicator, into which collection container indicator may be discharged from the indicator chamber.

The membrane may be made up of a single layer or multiple layers. It may have an outer coating, i.e., a coating applied to one side of the membrane that faces away from the indicator chamber, which coating provides desired functions. For example, the outer coating may serve to influence the ability of the membrane to be wetted by a measuring fluid, and/or to suppress the accumulation of unwanted substances, e.g., of microorganisms such as bacteria, other single-celled organisms, or algae (i.e., biofouling). The coating may also be designed to facilitate the diffusion of analyte through the membrane, and/or to prevent the diffusion of substances that would have a disruptive effect on the measurement through the membrane into the indicator chamber. The outer coating may also comprise an opaque layer that does not transmit radiation of a wavelength range of the radiation source, or radiation of a wavelength range that the radiation receiver can receive. In this way, the adulteration of the measurement due to external radiation penetrating into the indicator chamber is prevented.

The membrane may, additionally or alternatively, have an inner coating, i.e., a coating arranged on the side of the membrane facing towards the indicator chamber. For example, this may serve to counteract an aggregation of the species of the AIE-active substance due to accumulation at the interface between the membrane and the indicator contained in the indicator chamber. For example, this coating may comprise polyethylene glycol (PEG). The entire inner wall of the indicator chamber may additionally have such a coating, e.g., comprising PEG.

The measurement probe may additionally comprise an ultrasound source, such as an ultrasound source integrated into the sensor capsule. The ultrasound source may serve to radiate ultrasound waves into the indicator chamber to achieve a homogenization of the indicator, so that developed aggregates may be dissolved again if necessary. This improves the reversibility of the AIE effect exploited for the measurement, and accelerates the reaction time of the sensor.

The indicator may comprise an indicator solution. For example, the indicator may be formed as an indicator solution. For example, the indicator solution may comprise water or an ionic liquid as a solvent for the AIE-active substance.

In addition to the true solvent, the indicator solution may comprise at least one additional auxiliary substance which increases the solubility of the AIE-active substance and/or influences the viscosity of the indicator and/or decreases a boiling temperature of the indicator. A surfactant may be such an auxiliary substance, for example.

To set an essentially constant pH value of the indicator, said indicator may comprise an inorganic or organic pH buffer.

In an advantageous embodiment, the components of the indicator are chosen so that the indicator is temperature-stable up to a temperature of at least 120° C., or at least 140° C., and/or remains stable upon irradiation with gamma radiation of more than 5 kilogray (kGy), more than 25 kGy or more than 50 kGy.

The invention also encompasses an arrangement having an optical measurement probe according to one of the embodiments described in the preceding, and a superordinate unit connected to the measurement probe, wherein the measurement probe and the superordinate unit are coupled with one another via a releasable connection, and wherein energy is transmitted uni-directionally from the superordinate unit to the measurement probe via the connection.

The connection may advantageously be a galvanically-isolated connection, e.g., an inductively-coupled plug connector coupling and/or a radio connection.

The superordinate unit may, for example, be a measuring transducer, control electronics, or a power supply. It may comprise in a data processing unit, wherein additional data, such as the measurand, are transmitted bi-directionally between the measurement probe and the superordinate data processing unit via the connection.

BRIEF DESCRIPTION OF THE DRAWINGS

The invention is explained in further detail below on the basis of the exemplary embodiments shown in the figures. Shown are.

DETAILED DESCRIPTION

Figure 1:
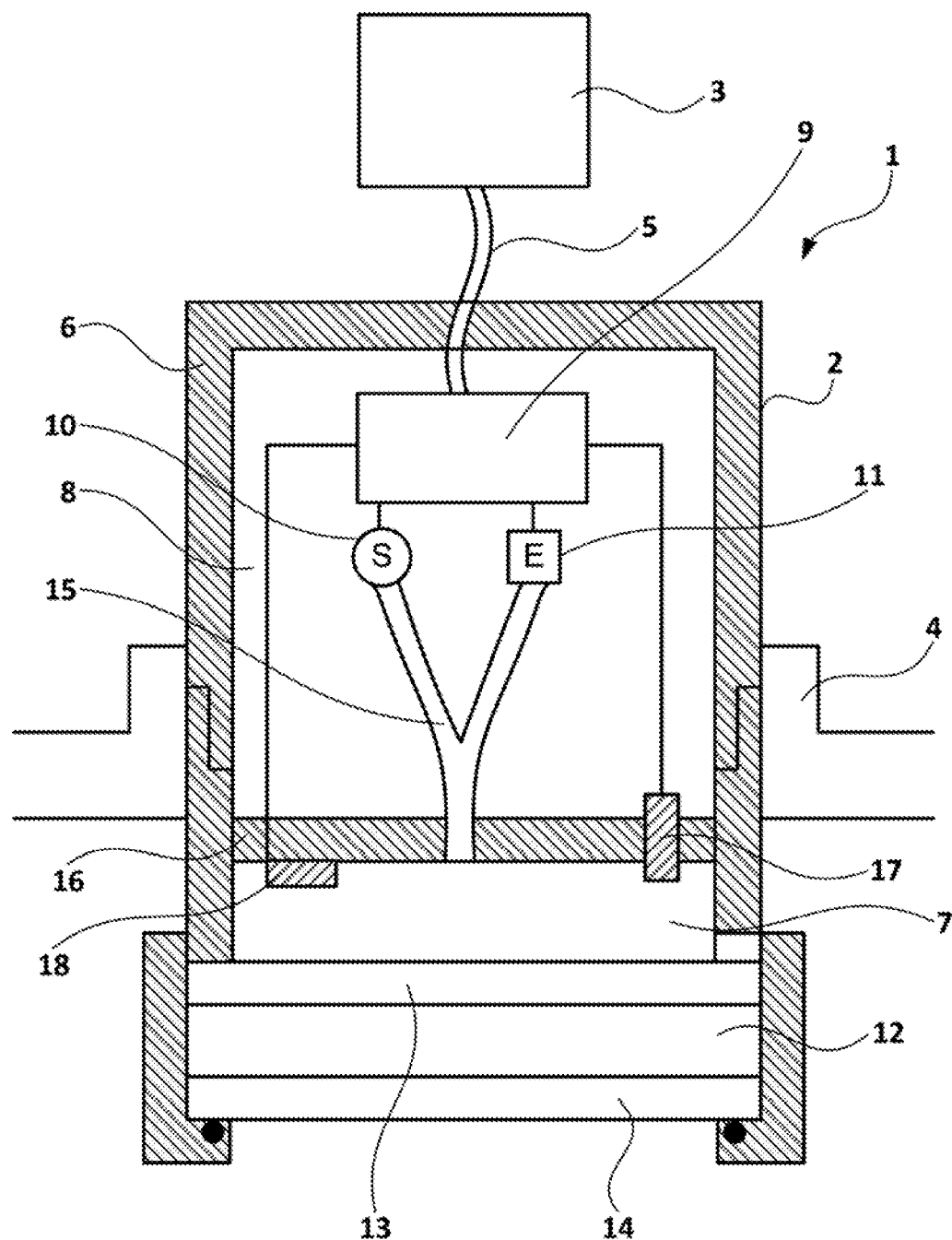
FIG. 1 shows an inline sensor in longitudinal section presentation, with a measurement probe according to a first exemplary embodiment.

An inline sensor 1 having a measurement probe 2 and a data processing unit 3 offset from the measurement probe is schematically depicted in FIG. 1. Alternatively, the data processing unit 3 may also be directly connected to the measurement probe 2 and/or be integrated into this. The measurement probe 2 is integrated into a wall 4 of a process vessel, for example, of a pipeline of a chemical production plant. For example, the measurement probe 2 may be fixed in a fitting connected to the wall. A segment of the measurement probe 2 that protrudes into the process vessel serves as an immersion region of the measurement probe 2 that comes into contact with a measurement fluid contained in the process vessel.

The data processing unit 3 comprises electronics that, for processing of signals and/or data that the measurement probe 2 outputs via a cable connection 5 to the data processing unit 3, may receive and further process. Alternatively, connection between the measurement probe 2 and the data processing unit 3 may also be realized wirelessly, for example, via inductive coupling and/or radio. The data processing unit 3 may have input means, e.g., buttons or one or more switches, by means of which a user may input information or commands to the electronics, for example, to operate the data processing unit 3 or the measurement probe 2. The data processing unit 3 may have additional output means, e.g., a display for locally showing measurement values, signals, or other information at the measurement location, and/or communication means, e.g., a communication circuit designed to output signals, e.g., digital signals. Via the communication means, the data processing unit 3 may be connected to a remote superordinate unit that is designed to communicate with said data processing unit 3 in a wired or wireless manner. The superordinate unit may, for example, be an operator device or a process controller, for example, a process control computer and/or a stored program control (SPS). The superordinate unit may also be a wearable operator device, for example, a smartphone or a tablet PC, or a flight-capable drone.

The measurement probe 2 comprises a probe housing 6 in which are formed, in the present example, two chambers 7, 8. A first chamber forms an indicator chamber 7 in which is contained a fluid indicator solution serving as an indicator of the measurement probe 2. A second chamber forms an electronics chamber 8 in which are arranged a sensor circuit 9, a radiation source 10, a radiation receiver 11, and a thermally-conductive temperature sensor 17 connected to the indicator. The sensor circuit 9 is electrically connected via the cable 5 to the data processing unit 3, as well as to the radiation source 10, the radiation receiver 11, and the temperature sensor 17, and is designed to control the radiation source 10, to receive and process signals of the radiation receiver 11 and of the temperature sensor 17, and to output processed signals to the data processing unit 3. The radiation source 10 may comprise a UV flash lamp or one or more LED's, which preferably emit radiation in the visible range. The radiation receiver 11 may, for example, comprise one or more photoelectric transducers, e.g., one or more photodiodes, a CCD line, or a CCD array. The temperature sensor 17 may comprise a temperature-dependent measurement resistor, for example. In a further exemplary embodiment, in addition to the temperature sensor 17, a pressure sensor (not shown) designed to detect the pressure prevailing in the indicator chamber 7 may also be provided that, for example, may be arranged in the indicator chamber 7 or in a chamber fluidically connected to the indicator chamber 7. In this instance, the pressure sensor is likewise connected to the sensor circuit 9, which then is additionally designed to receive and process signals output by the pressure sensor to the sensor circuit 9.

Moreover, arranged in the electronics chamber 8 are optical waveguides 15 that transmit radiation of the radiation source 10 into the indicator chamber 7 through a wall 16 separating the indicator chamber 7 from the electronics chamber 8. The optical waveguides 15, moreover, transmit radiation from the indicator chamber 7 to the radiation receiver 11.

At its end facing towards the process vessel, the indicator chamber 7 is closed by a membrane 12. In the example depicted in FIG. 1, the membrane 12 has an inner coating 13 on its side facing towards the indicator chamber 7 and an outer coating 14 on its side facing away from the indicator chamber 7. The outer coating 14 is in contact with the measuring fluid; the inner coating 13 is in contact with the indicator contained in the indicator chamber 7.

The indicator generates an optical signal, e.g., a fluorescence radiation, using which the measurand to be determined by the inline sensor 1 can be ascertained. For example, the measurand may be a concentration of an analyte in a measuring fluid, or a different measurand, for example, a pressure or a temperature. In the following, the functionality is described using the determination of an analyte concentration. In principle, however, the description in the following can also be transferred to a pressure measurement or temperature measurement.

To determine an analyte concentration in a measuring fluid, the membrane 12 includes the inner coating 13 and the outer coating 14 such that it is permeable to the measuring fluid, or at least to the analyte. The analyte may thus penetrate into the indicator chamber 7 and also leave the indicator chamber 7 again. In this way, it is ensured that, in the indicator chamber 7, an equilibrium concentration of the analyte always appears that corresponds to an equilibrium concentration outside of the indicator chamber.

As explained above, the indicator comprises an AIE-active substance. The luminescence intensity of the AIE-active substance or of the indicator that is present in the indicator chamber 7 consequently depends upon the extent of the formation of aggregates in the indicator in which species of the AIE-active substance participate. Different approaches are possible here, for example: a self-aggregation of the species of the AIE-active substance is disrupted by the analyte, e.g., in that an existing aggregate is disrupted by the influence of the analyte; or a self-aggregation of the species of the AIE-active substance is promoted by the analyte; or aggregates of the chemical species (for example, ions, molecules) of the analyte form with the chemical species of the AIE-active substance.

In order to reduce the response time of the measurement probe 2, i.e., in order to accelerate the appearance of equilibrium concentrations, the measurement probe 2 may comprise means for agitating the indicator contained in the indicator chamber 7, e.g., a stirrer or—as in the present exemplary embodiment of FIG. 1—an ultrasound source 18 that radiates ultrasound waves into the indicator, such that the ultrasound waves produce an agitating effect in the indicator. The means of agitation (here, the ultrasound source 18) may be supplied with power and controlled via the sensor circuit 9. An appearance of concentration equilibriums may be accelerated in this way. In this way, the deposition of aggregates on the wall bordering the indicator chamber 7, such as the coated membrane 12, may also, additionally, be prevented. In instances in which the aggregates do not easily detach again with the participation of the AIE-active species if the analyte concentration changes, i.e., when the aggregation is not reversible without further measures, a reversibility may be achieved in that the ultrasound source 18 or, insofar as it is present, an agitator is used in a pulsed manner. In this way, the detachment of the aggregates may be accelerated again if the concentration of the analyte in the measuring medium changes, for example, decreases.

In the present example, the measurement probe 2 is embodied to detect a fluorescence intensity of the indicator. For this, excitation radiation is conducted via the optical waveguide 15 into the indicator chamber 7 from the radiation source 10. The excitation wavelengths are preferably in a range between 200 and 2,000 nm. The excitation radiation excites a fluorescence of the aggregates in the indicator that contain the AIE-active substance. A portion of the fluorescence radiation thereby emitted is captured via the optical waveguide 15 and guided to the radiation receiver 11. Using the receiver signal, an electrical signal that is output to the sensor circuit 9 as a primary signal dependent upon the measurand may be generated in a known manner, e.g., via measurements of an intensity or of an intensity change, an intensity ratio between the fluorescence radiation and a reference radiation, a phase angle, or in another way. In the sensor circuit 9, the primary signal is processed further, e.g., amplified and/or digitized, and the processed primary signal is output via the cable 5 to the data processing unit 3 as a measurement signal representing a measurement value of the measurand. The data processing unit 3 may further process the measurement signal itself and determine from this a measurement value, derive other signals from the measurement signal, and/or output the measurement signal, the measurement value or other signals derived from the measurement signal via a display, and/or relay them to a superordinate unit. The determination of the measurement value from the primary signal may, for example, take place using an association rule determined via calibration, for example, a calibration function (calibration line) or a table. This may be stored in a memory of the data processing unit 3. By means of the temperature measurement signal provided by the temperature sensor 17, the sensor circuit 9 or the data processing unit 3 may perform a temperature compensation of the measurement signal or of the measurement value determined from the measurement signal. If a pressure sensor is present, the pressure measurement signal may also be taken into account in the measurement value determination.

In principle, depending upon the selection of the indicator and/or of the membrane, with the inline sensor 1, the concentration of a plurality of chemical analytes, biological substances, or physical parameters may be determined, e.g., the concentration of ions such as hypochlorite or hypobromite; of inorganic molecules such as water (or humidity), hydrogen peroxide; of organic molecules such as glucose, fructose, lactose, enzymes; a concentration or a number of living and/or dead cells; concentrations of solvents such as water, hexane, heptane, or fluorine compounds. Gas concentrations may also be determined with the sensor 1, such as concentrations of gases dissolved in water, e.g., carbon dioxide, oxygen, nitrogen oxides, and or ozone.

In addition to analyte concentrations, additional measurands influencing the aggregation of the AIE-active substance, e.g., pressure or temperature, may be determined by means of such an inline sensor. If the measurand is not an analyte concentration, an influence of the measurand, e.g., a temperature influence and/or pressure influence, on the self-aggregation of the chemical species of the AIE-active substance may, accordingly, be used for the measurement. This may also be used to determine, in the inline sensor 1 depicted in FIG. 1, temperature and/or pressure for a temperature and/or pressure compensation of the measurement value of the measurand (analyte concentration) to be determined by the inline sensor 1. In this instance, the measurand 2 may contain one or more additional AIE-active substances whose self-aggregation is influenced by pressure and/or temperature. These may be contained in the indicator chamber 7. An AIE-active substance serving for temperature measurement may also be arranged in an additional housing chamber within the measurement probe 2 that is connected to the indicator chamber 7 in a thermally-conductive manner, for example, via a wall having good thermal conductivity. An AIE-active substance serving for pressure measurement in the indicator chamber may be contained in an additional housing chamber connected to the indicator chamber via an elastic wall. The one or more additional AIE-active substances for pressure or temperature measurement may be connected via optical waveguides to a radiation source contained in the measurement probe and a radiation receiver, such that temperature measurement values or pressure measurement values may be determined using luminescence measurements. For example, signals of the radiation receiver 11 may be detected and processed by the sensor circuit 9 or the superordinate data processing unit 3. The sensor circuit 9 or the data processing unit 3 may use the temperature measurement values and pressure measurement values for compensation of the measurement values of the analyte concentration.

In the example described here, the species of the AIE-active substance, which may be molecules or complex compounds, for example, are present dissolved in the indicator solution contained in the indicator chamber 7, such that luminescent aggregates cannot unintentionally form due to breakdown of the species. The solubility of the AIE-active substance in the solvent of the indicator solution may be increased by functional groups bound to the species of the AIE-active substance. In the present example, the indicator solution is an aqueous solution. Suitable functional groups for increasing the water solubility of the AIE-active substance are, for example, low-molecular groups such as sulfonic acid groups, carboxylic acid groups, phosphoric acid groups, hydroxy groups, histamine groups, imidazole groups, benzimidazole groups, pyridine groups, amine groups, and/or zwitterionic functional groups. Examples of zwitterionic functional groups are quaternary amines with acid or acid ester group, such as propane dimethyl aminopropane sulfonic acid groups, propane dimethyl aminopropane phosphoric acid groups, propane dimethyl aminopropane boric acid groups, propane dimethyl aminopropane butyric acid, such groups with greater or lesser alkyl chain lengths, or lecithin ((R)-1-oleoyl-2-palmitoyl-phosphatidyl-choline).

A functionalization of the aggregates is also possible with higher-molecular groups, such as peptides, that can themselves contribute to aggregation. AIE-active species that are insoluble or only poorly soluble in water may also be brought into solution via masking, for example, in the form of water-soluble complex compounds in an aqueous indicator solution. The use of AIE dots is also possible. These may be particles, such as nanoparticles, in which species of an AIE-active substance are embedded or covalently integrated. The species of the AIE-active substance may, for example, be encapsulated in a casing of water-soluble molecules and/or in a water-soluble polymer. It is advantageous to integrate the species of the AIE-active substance into a polymer, for example, into a primary chain or side chain or into dendrimers. All structures are advantageous that promote a solubility in a solvent, e.g., water, but simultaneously allow the formation of aggregates with participation of the species of the AIE-active substance.

The solubility of the AIE-active substance in the indicator solution may also be increased by auxiliary substances contained in the indicator solution. For example, triazoles, imidazoles, pyridines, polyols such as polyglycerol or substances with polyglycerol groups, dendrimers, polyethylene glycol, polypropylene glycol, or zwitterions may be considered as masking agents or auxiliary substances for increasing the solubility of the AIE-active substance in an indicator solution based upon water as a solvent.

The indicator solution may also comprise substances with sulfonic acid groups, sulfonic acid, phosphoric acid, and/or amines to improve the water solubility of the AIE-active substance.

The amines may, advantageously, be present as soluble zwitterions, for example, di allyldimethylammonium chloride (DADMAC). Additional water-soluble auxiliary substances that may improve the solubility of AIE-active species in an aqueous solution are heparin, triazones, histidines, amino acids, DNA, and carbazoles.

It may be advantageous to dissolve the AIE-active substance in a solvent immiscible with water, in which solvent the analyte is also soluble. If the analyte is an ion or another polar substance, an ionic fluid may be considered as a solvent, for example. Ionic fluids are an advantageous solvent if the water solubility of the AIE-active substance is too low and also cannot be increased to a sufficient degree via use of auxiliary substances.

AIE-active substances that are not water-soluble may also be held in solution in an aqueous indicator solution via micelle formation with the aid of a surface-active substance. In a special embodiment, the AIE-active substance may also itself be a surface-active substance or a surfactant, which may itself form micelles in an aqueous solution without participation of additional auxiliary substances. Conceivable are simple micelles, double micelles, and additional variants of micelles known to the person skilled in the art, e.g., spherical micelles, reversible micelles, cylindrical micelles, vesicles, lamellae, organized structures at phase boundaries, or bicontinuous structures. Surface-active auxiliary substances or surface-active AIE-active substances have a polar part and a non-polar part that arrange themselves under micelle formation in solution. One example of an AIE-active substance that can be applied in sensor 1 and that is simultaneously surface-active, and thus is present dissolved in an aqueous indicator solution via micelle formation, is TPE-SDS 1,2-distearoyl-sn-glycero-3-phosphoethanolamine.

Suitable surfactants that, as surface-active auxiliary substances in the indicator solution, may hold the AIE-active species that is not water-soluble in solution by micelle formation are: alkylphenol ethoxylates, alcohol ethoxylates, alkyl ethoxylates, alkylamide ethoxylates, alkyl aminoethoxylates, alkyl glucosides, sorbitan alkanoates, ethoxylated sorbitan, alkanoates, alkane and alkene amine salts, alkylquat salts, alkyl- or alkene diamine salts, dialkylquat salts, esterquat salts, betaines, amidobetaines, imidazolines, amine oxides, alkyl glycosides, or ethoxylated monoethanolamides of long-chain fatty acids. For example, N-[methoxy(polyethylene glycol)-2000] (DSPE-PEG2000) and DSPE-PEG5000-folate are suitable micelle creators.

The indicator solution may also be present in the indicator chamber in thickened form, as a free-flowing gel or as a non-free-flowing gel. Instead of water as a solvent, the indicator solution contained in the indicator chamber 7 may also be based upon an ionic liquid as a solvent. In all of these instances, the indicator solution may likewise contain auxiliary substances for improving the solubility of the AIE-active substance in the indicator solution.

Auxiliary substances may also be present in the indicator solution in order to keep the viscosity of the solution constant, to keep the pH value constant, or to decrease the vapor pressure of the solution.

For example, anionic copolymers of methacrylic acid and methmethylacrylate (Eudragit) may be considered as means for controlling the pH value, such as with pH values in the neutral and alkaline pH range. Dendritic polyglycerols or polyglycerol sulfonates may be considered as auxiliary substances for adjusting and controlling a desired viscosity of the indicator solution.

For example, the indicator solution may be based upon an aqueous solution that is thickened with an organic or inorganic polymer. In this instance, an additional pH buffer may be added to the indicator solution, e.g., a harmless inorganic buffer, or the polymer added to thicken the indicator solution may be selected so that it simultaneously serves as a pH buffer. The pH value may be, advantageously, more than 10 or less than 8.5. Suitable as buffers for this purpose are, for example, carbonate buffers, polyacrylic acid, polyacrylic acid-histamine copolymers, histamine-amine copolymers, or a Britton-Robinson buffer (for example, produced from 0.0286 M citric acid, 0.0286 M potassium dihydrogen phosphate, 0.0286 M boric acid, 0.0286 M barbital, and 0.0286 M HCl, and brought to the desired pH value via titration with 0.02 M NaOH).

The indicator solution may additionally contain one or more auxiliary substances that reduce the effect of temperature changes on properties of the indicator solution, for example, on its viscosity. Changes in the viscosity that are too strong may influence the aggregate formation and dissolution, and thus produce a change in the signal strength and/or the response time. For example, acrylamides such as PNIPAm (poly-n-isopropylacrylamide) may be considered as such an auxiliary substance.

The AIE-active substance present in the indicator solution is, advantageously, selected so that the species of the AIE-active substance, which possibly are modified with the aforementioned functional groups to improve the solubility, exhibit no, or at least only a slight, self-luminescence in the base state.

Mixtures of AIE-active substances may also be used as an indicator, wherein, in this case, preferred derivatives of similar molecular structures are used. For example, an indicator may thus contain a mixture of AIE-active substances of the same material group, wherein molecules of a first AIE-active substance contained in the indicator have functional groups that serve as receptor locations for the analyte, whereas molecules of a second AIE-active substance contained in the indicator have no such functional groups, but otherwise correspond with the molecules of the first AIE-active substance. Preferably, different concentrations of the individual components of the mixture may be used. However, one of the components is, ideally, the main component.

The embodiment of the membrane 12, and possibly of coatings applied thereon, depends upon what measurand is to be detected by the inline sensor 1. If an analyte concentration or a measurand dependent upon an analyte concentration is to be determined, the membrane 12 may be permeable to the measuring fluid or to an analyte contained in the measuring fluid. A permeability may be achieved by the membrane having pores through which the analyte may pass. Alternatively, the membrane 12 may be comprised of a material, e.g., a polymer, that is permeable to the analyte, and be of correspondingly thin design.

Both hydrophilic and hydrophobic membranes are suitable, which are used according to the application; if the analyte is a gas, e.g., oxygen, hydrophobic membranes are preferably used, whereas hydrophilic membranes may preferably be used for determining analyte concentrations of ionic or polar analytes, e.g., pH value, $CO_2$, glucose, or a cell measurement. The membrane 12 ideally has as large an area as possible, whereby a large exchange with the measuring fluid takes place. The membrane may thus be aligned in both the axial direction and radial direction.

For example, the membrane may be formed as a polymer membrane whose base material is selected so that it is largely chemically inert relative to the measuring fluid or components of the measuring fluid, and withstands temperatures occurring in a heat sterilization, i.e., temperatures above 120° C. or above 140° C.

Examples of hydrophobic polymer membranes that withstand the cited temperature conditions and are sufficiently chemically inert are the following finely-porous or non-porous polytetrafluoroethylene, (PTFE), polyvinylene difluoride (PVDF), polyethylene tetrafluoroethylene (ETFE), copolymers of tetrafluorethylene (TFE) and perfluoralkoxyvinylethers (PFA), fluorinated ethylene-propylene copolymers (FEP), polyvinyl fluoride (PVF), polychlorotrifluoroethylene (PCTFE), polyethylene chlorotrifluoroethylene (ECTFE), tetrafluoroethylene propylene (FEPM), perfluoropolyether (PEPE), perfluorosulfonic acid (PFSA), perfluoropolyoxetanes, silcones, perfluorinated and partially fluorinated silicones.

Examples of hydrophilic membranes, such as polymer membranes, that withstand the cited temperature conditions and are sufficiently chemically inert are the following: siloxanes with side chains such as polyethylene glycol, polyglycerol, zwitterions, etc., Nafion, propane-dimethylamine-propane sulfonic acid trimethoxysilanes, propane-dimethylamine-propane phosphoric acid trimethoxysilanes, propane-dimethylamine-propane boric acid trimethoxysilanes, propane-dimethylamine-propane butyric acid trimethoxysilanes, propane-dimethylamine-propane sulfonic acid triethoxysilanes, propane-dimethylamine-sulfonic acid triethoxysilanes, amorphous silica particles, polyurethane, silicone, cellulose and its derivatives such as cellulose acetate, imidazole derivatives Solgel (Xerogel), polyphenol, graphene oxide.

According to the present disclosure, due to the high mechanical stability, a ceramic structure which is provided on its inside with a deposit-repelling coating may also be used as a membrane. A polymer forming the membrane, or a polymer applied as an inner coating to the membrane, may be modified by side chains such that an agglomeration of indicator components on the side of the membrane facing towards the indicator chamber is hindered.

In an example, the membrane 12 may be formed from a polymer membrane that is permeable to the analyte. In this example, the membrane 12 is connected fluid-tight to the remaining probe housing 2. However, a multitude of alternative embodiments are possible. For example, the membrane may also be designed as a porous wall of the probe housing, e.g., via a wall region sealing the indicator chamber 7 and having one or more through-holes, e.g., nano-holes, via a wall or layer sealing the indicator chamber 7 and made of a porous and/or ion-conductive substance, for example, comprising a molecular sieve, a zeolite, a ceramic, an ion exchanger, a proton conductor, an MOF (Metal Organic Framework) or a ZIF (Zeolitic Imidazolate Framework). The membrane or the wall region may be designed as one piece with the probe housing, or be firmly connected to the probe housing. The membrane may also be a component of a membrane cap that can be connected to a probe body so as to be releasable. In this embodiment, the probe body and the membrane cap together form the probe housing, and the membrane cap seals the probe housing and the indicator chamber formed therein against the measuring medium. If the membrane is made of a porous material, e.g., a porous ceramic or zeolite, it may be made in the form of a cap partially or entirely comprised of the porous material, which cap is connected to the probe body (for example, via a plug or screw connection) so as to be releasable, so that the cap seals the indicator chamber at the measuring medium side. In this embodiment, a faster analyte exchange is possible between the measuring fluid and the indicator contained in the indicator chamber. It is here advantageous if the auxiliary substances that are possibly contained in the indicator solution cannot pass the membrane in the direction of the measuring medium. As mentioned, the porous ceramic may be provided on its outside with an analyte-selective (polymer) coating and/or on its inside with a deposit-repelling coating.

The outer coating 14 applied to the outside of the membrane 12 in the example depicted here may serve various purposes. On the one hand, it may prevent an agglomeration of air bubbles or possess an anti-fouling effect. On the other hand, it may prevent the escape of species of the AIE-active substance from the indicator chamber into the measuring fluid. Additionally or alternatively, the outer coating 14 may serve to increase the selectivity of the sensor in that it, essentially, selectively lets the analyte pass out of the measuring fluid into the membrane 12.

A selectivity of the membrane 12, or of the outer coating 14, for a specific analyte may, for example, be ensured via pores in the membrane 12 and/or in the outer coating 14, whose size is chosen such that the analyte may selectively pass through the outer coating 14 and/or the membrane 12.

In order to increase the selectivity of a membrane 12 to glucose, it may, for example, be provided with an outer coating 14 that is formed from one of the following materials: zwitterions, such as propane-dimethylamine-propane sulfonic acid trimethoxysilane, propane-dimethylamine-propane phosphoric acid trimethoxysilane, propane-dimethylamine-propane boric acid trimethoxysilane, propane-dimethylamine-propane butyric acid trimethoxysilane, propane-dimethylamine-propane sulfonic acid triethoxysilane, propane-dimethylamine sulfonic acid triethoxysilane, cyanuric chloride derivative of caldarchaeol, hydrophobic silica particles, ceramic nanoparticles, imidazole derivatives, or amorphous silica particles with quaternary ammonium ions.

The inner coating 13 of the membrane 12 may be designed to prevent the agglomeration of aggregates with participation of the species of the AIE-active substance at the interface between the indicator solution contained in the indicator chamber 7 and the membrane 12 provided with the inner coating 13. For example, an inner coating made of a polyethylene glycol siloxane is suitable for this purpose. It is also possible to provide the entire wall of the indicator chamber 7 that is in contact with the indicator with such a coating. In an alternative embodiment, to avoid an agglomeration of aggregates on the wall or membrane bordering the indicator chamber 7, instead of a coating, the material of the wall or membrane may be functionalized with functional groups that suppress aggregation.

Functional groups that do not promote aggregation, but rather prevent it, are suitable for such a coating or for functionalization of materials in contact with the indicator. Particularly preferred are molecules or side chains which are flexible and/or induce no particular organization in auxiliary substances in the indicator solvent or added to the indicator.

The following substances and/or functional groups are cited as examples: polyethylene glycol (PEG) and PEG derivatives such as esters, ethers, imidazoles, zwitterions; ampholytes with zwitterions; polyglycerols and their derivatives; polypropylene glycols (PPG) and PPG derivatives; polymers having branched side chains, such as farnesols; phenolates; dendrimers or highly-branched polymers (technical term: hyperbranched polymers), such as polyglycerols; siloxanes or urethanes having branched side groups; siloxanes having alkylphosphate, alkylsulfonate, or alkylcarbonate groups; siloxanes or urethanes having alkylether phosphate, alkylether carbonate, alkylether sulfonate groups; siloxanes having lecithin groups; dialkylsulfosuccinates; and side chains having amines such as spermidines or amine analogs to PEG or short-chain polyether imides, polyamidoamines, or modified trimethoxymethylsilylpropyl (polyethylenimine).

These substances for preventing the formation of unwanted aggregates with participation of the species of the AIE-active substance at the walls of the indicator chamber are, advantageously, at least partially soluble or capable of swelling or capable of being wetted well in the solvent of the indicator solution.

In the embodiment of FIG. 1, the indicator chamber 7 is designed as a chamber in the probe housing 2 that is open towards the forward end of the measurement probe 2, which chamber is sealed by the membrane 12 coated on both sides so that a material exchange with a measuring medium contacting the measurement probe 2 at its forward end region (immersion region) may take place across the membrane 12. In an alternative advantageous embodiment, the membrane 12 and possibly also the indicator chamber 7 are arranged in an exchangeable sensor cap that is connected, so as to be releasable, to a probe body to form the probe housing. This allows a regular exchange of the membrane and of the indicator contained in the indicator chamber.

Additional advantageous embodiments are conceivable, some of which will be described in detail in the following. For example, the measurement probe 2 may have an inlet opening into the indicator chamber 7 and an outlet that is likewise fluidically connected to the indicator chamber 7. This enables the indicator to be changed from time to time or continuously. The indicator may thereby be discarded after being conducted out of the indicator chamber, or may be directed back into the indicator chamber again via a loop. The indicator may, if necessary, be subjected to a regeneration before the return feed.

Figure 2:
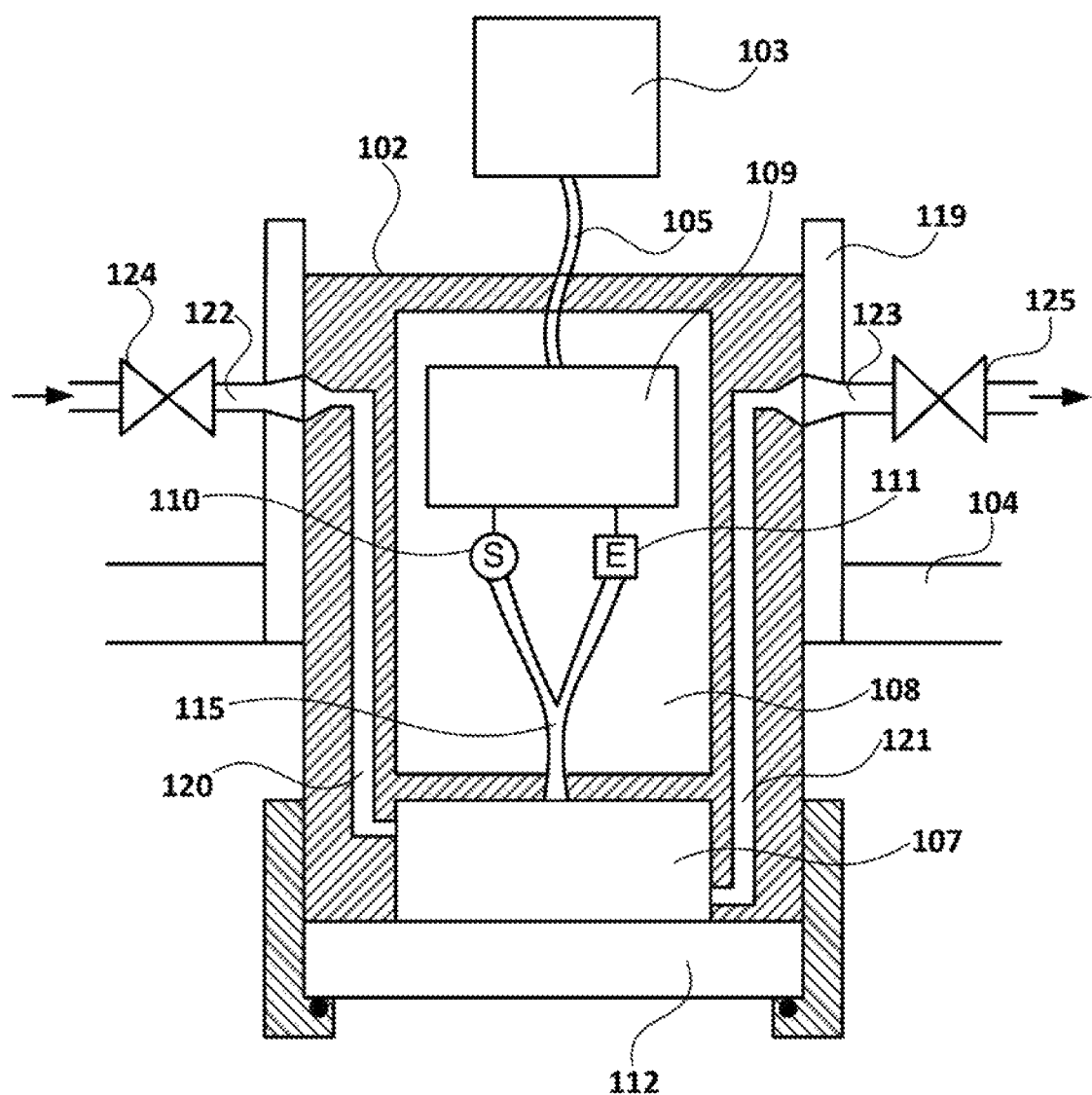
FIG. 2 shows a measurement probe in longitudinal section presentation, according to a second exemplary embodiment.

In FIG. 2, as an additional exemplary embodiment of the present disclosure, a measurement probe 102 of an inline sensor 101 for optical determination of an analyte concentration is schematically depicted in longitudinal section. The measurement probe 102 has a housing in which two chambers 107, 108 are formed. Analogously to the measurement probe 2 depicted in FIG. 1, the housing of the measurement probe 102 can be integrated using a fitting 119 into a wall of a process vessel 104. One of the chambers formed in the housing forms an electronics chamber 108 in which are arranged a sensor circuit 109, a radiation source 110, and a radiation receiver 111. The sensor circuit 109 is connected via a conductor 105 to a data processing unit 103 for communication. The data processing unit 103, moreover, supplies the sensor circuit 109 with power. The sensor circuit 109, the radiation source 110, and the radiation receiver 111 may be designed analogously to the corresponding parts of the measurement probe depicted in FIG. 1. The second chamber forms an indicator chamber 107 that serves to receive an indicator containing an AIE-active substance, for example, an indicator solution according to one of the compositions described above in connection with FIG. 1 and measurement probe 2. At its front-side end embodied for immersion into the measuring medium, the housing is terminated by a membrane 112 sealing the indicator chamber 107. The membrane 112 may be formed from a polymer that is selectively permeable and may possibly comprise multiple layers.

The radiation source 110 and the radiation receiver 111 are connected to the indicator chamber 107 via optical waveguides 115 to radiate excitation radiation into the indicator, and to guide luminescence radiation emitted by the indicator to the radiation receiver 111. In the housing wall of the measurement probe 102, fluid conduits 120, 121 are formed that open at one end into the indicator chamber 107, and, at their other end, are open to the environment of the measurement probe 102. These open ends may comprise terminals for connection to additional fluid conduits. The terminals may, advantageously, comprise valves by which a fluid transport into the indicator chamber 107 and/or out of the indicator chamber 107 may be prevented. In the present example, the measurement probe 102 is integrated into the housing wall using the fitting 119, which housing wall has additional conduits 122, 123 matching the fluid conduits 120, 121, such that the additional conduits 122, 123 may be fluidically connected to the fluid conduits 120, 121. For its part, a first of the additional conduits is connected to a first reservoir in which is contained a reserve of the indicator comprising the AIE-active substance. It serves as a supply line 122 for indicator into the indicator chamber 107. The second of the additional conduits is connected to a second reservoir and serves as a discharge line 123 for consumed indicator out of the indicator chamber into the second reservoir.

In the embodiment of FIG. 2, the supply line 122 and discharge line 123 can be sealed by the valves 124, 125. Pumps interacting with fluid conduits, or pneumatics or hydraulics acting on the reservoirs, may serve for fluid transport. An automatic control of the fluid inlet and outlet in the indicator chamber 107 may take place via the sensor circuit 109, the data processing unit 103, or an additional external controller. In the last instance, for communication, the external control may be connected to the sensor circuit 109 and/or the data processing unit 103 so that the measurement value detection may be synchronized with the exchange of the indicator in the indicator chamber 107. The measurement probe 102 may advantageously comprise a pressure sensor that detects the pressure prevailing in the indicator chamber 107. The signal of the pressure sensor may be used to control the fluid transport through the indicator chamber. The pressure in the indicator chamber 107 should ideally remain essentially constant during the measurement operation.

The measurement probe 102 may additionally comprise above a temperature sensor and/or means for agitation of the indicator located in the indicator chamber 107.

Due to the indicator chamber 107 being connected to a reservoir having an indicator reserve, the indicator located in the indicator chamber 107 may be exchanged or circulated from time to time, or even continuously. Such an embodiment has the advantage that, for example, measurement errors due to concentration changes in components of the indicator may be avoided in that essentially consistent concentrations are maintained via regular exchange of the indicator solution. As mentioned above, such concentration changes may, for example, be caused due to a degradation of individual components of the indicator solution due to thermal stress upon sterilization or due to irradiation with the excitation radiation of the radiation source.

In a further embodiment, the indicator solution may be directed back into the first reservoir or back into the indicator chamber 107 again in a loop after leaving the indicator chamber 107. A regeneration of the indicator solution, e.g., via homogenization, may be provided in the loop before the return into the indicator chamber 107.

The indicator chamber 107 may also be fluidically connected to multiple reservoirs via one or more inlets. For example, a first reservoir may contain an indicator for determining a concentration of a first analyte, e.g., a pH value, whereas a second reservoir contains a second indicator for determining a concentration of a second analyte, for example, glucose. The first or the second indicator may then, optionally, be directed into the indicator chamber, depending upon which analyte is to be measured. Since the first and second indicators possibly comprise different AIE-active substances, in this embodiment, the measurement probe may comprise multiple different radiation sources, to excite the different aggregates formed by the AIE-active substances to fluorescence with excitation radiation of different wavelengths. Alternatively, the measurement probe may also comprise a single radiation source that can emit radiation of different wavelengths (for example, a controllable LED). A switchable filter for the radiation emitted by the radiation source 110 is also possible, for selection of specific excitation wavelengths. In such embodiments, the sensor circuit 109 is designed to control the introduction of the indicator solution into the indicator chamber and the excitation of the fluorescence of aggregates of the AIE-active species in the indicator chamber in contact with the analyte, so that these are matched to one another. Alternatively, the sensor circuit 109 may be designed to receive signals of an external controller controlling the introduction of the indicator solution into the indicator chamber, and, using the received signals, to determine which indicator is currently located in the indicator chamber 107 and to accordingly select the associated excitation radiation of the radiation source 110. The sensor circuit 109 is, additionally, designed to determine the measurement values of the concentrations of the different analytes according to different calculation rules matched to the respective analyte or indicator, depending upon which indicator is presently located in the indicator chamber 107 at the point in time of detection of the measurement signal. If a change is made from one indicator to another, a flushing of the indicator chamber 107 may be performed intermittently.

Figure 3:
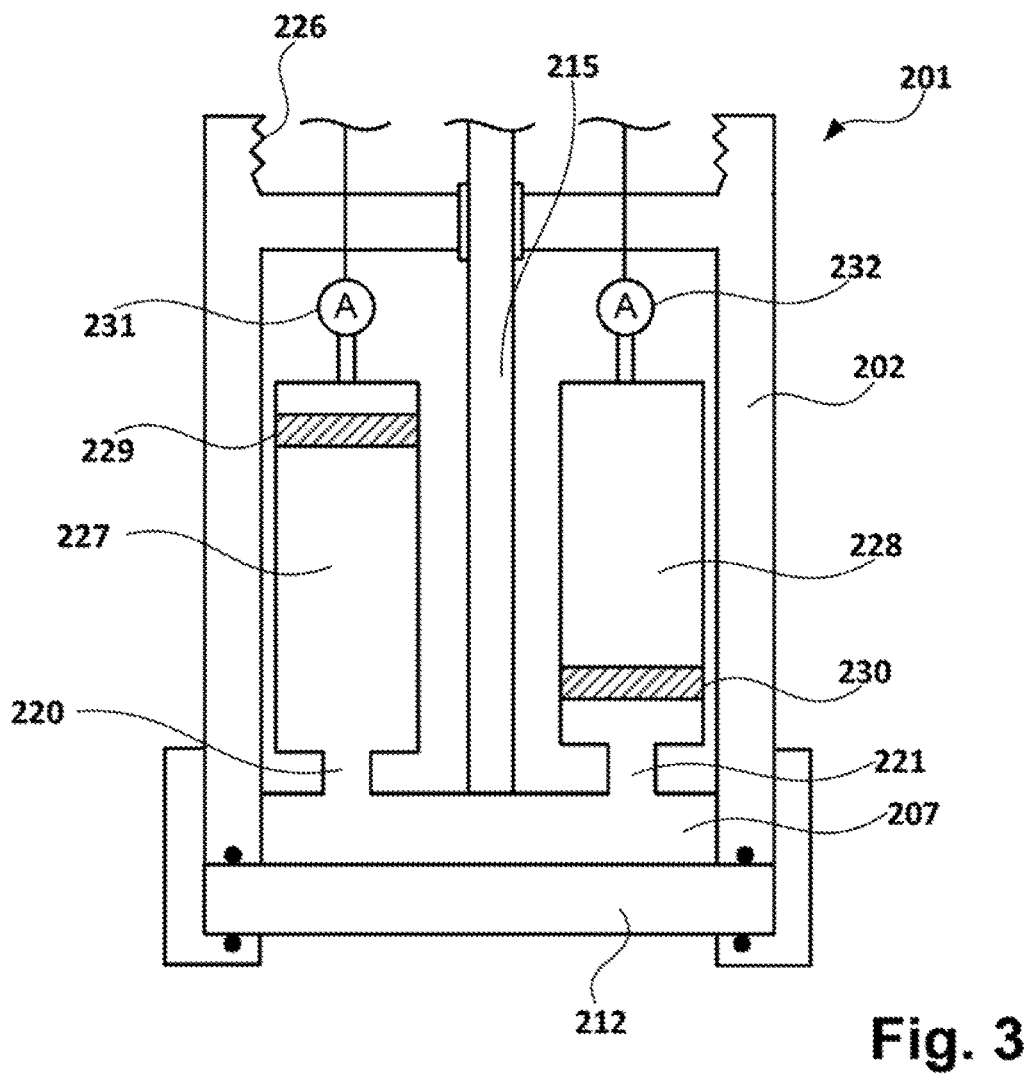
FIG. 3 shows a measurement probe in longitudinal section presentation, according to a third exemplary embodiment.

Schematically depicted in FIG. 3, in a longitudinal section presentation, is a sensor capsule 201 for a measurement probe of an inline sensor for optically determining an analyte concentration. The sensor capsule 201 possesses a housing 202 that has a thread 226 at its rear end. The thread 226 may be connected to a complementary thread of a probe body so as to be releasable. The probe body, which is not depicted in FIG. 3, comprises, within a housing that can be connected to the sensor capsule 201, a sensor circuit as well as a radiation source and a radiation receiver, which may be analogous to the corresponding parts of the measurement probe depicted in FIG. 1. Like these, the measurement probe formed from probe body and sensor capsule 201 may be connected to a data processing unit. Analogously to the measurement probe depicted in FIG. 1, the measurement probe can be integrated by means of a fitting into a wall of a process vessel.

The housing 202 contains an indicator chamber 207 terminated by a membrane 212. Arranged in the housing 202 are optical waveguides 215 that are directed out of the housing 202 through a rear lead-through, i.e., a lead-through arranged on a side of the sensor capsule 201 facing away from the membrane 212. Upon connection of the sensor capsule 201 to the probe body, they are connected to the radiation source contained therein and the radiation receiver contained in the probe body, for example via additional optical waveguides.

Moreover, a first reservoir 227 is formed in the housing 202, in which is present a reserve of indicator solution and which is connected via a supply line 220 to the indicator chamber 207. In the housing, a second reservoir 228 is formed to which the indicator chamber 207 is connected via a discharge line 221. The second reservoir 228 serves to receive used indicator solution discharged from the indicator chamber 207. The sensor capsule 201 may also comprise means for agitating the liquid present in the indicator chamber 207, as has already been described further above using the first exemplary embodiment. Both reservoirs 227, 228 may be cylindrical chambers in which, respectively, is arranged a piston movable along the cylinder axis, the outer diameter of which piston is matched to the cross-section of the cylindrical chambers such that the piston respectively separates a liquid-filled segment of the reservoirs 227, 228 that faces towards the indicator chamber 207 from a gas-filled segment of the reservoirs 227, 228 that faces away from the indicator chamber 207. The pistons 229, 230 are displaceable in the axial direction by one or more actuators 231, 232, e.g., pneumatic actuators, to transport indicator solution from the first reservoir 227 into the indicator chamber 207 and to simultaneously transport indicator solution from the indicator chamber 207 into the second reservoir 228. The actuators 231, 232 may be connected via lead-throughs to a gas source and/or power source outside of the sensor capsule 201. They can be controlled by control electronics arranged either in the probe body or outside of the measurement probe 201.

Figure 4:
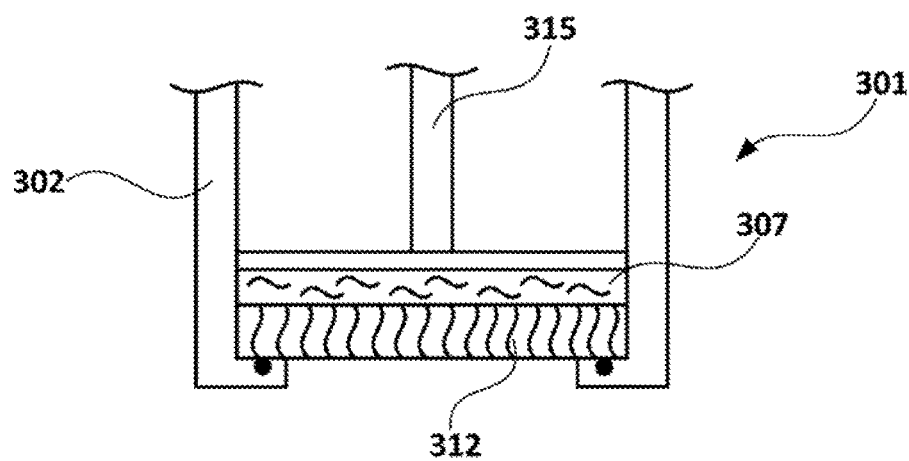
FIG. 4 shows a measurement probe in longitudinal section presentation, according to a fourth exemplary embodiment.

Schematically depicted in longitudinal section in FIG. 4 is the immersion region 301, designated for immersion into a measuring fluid, of a measurement probe according to a further exemplary embodiment. The immersion region 301 may be either a segment, facing towards the measuring fluid, of a sensor capsule which can be connected to a probe base body, similarly to the exemplary embodiment described using FIG. 3, or a forward end region of a measurement probe, similar to the measurement probe without detachable sensor capsule depicted in FIG. 1. The optical and electronic components of the measurement probe, i.e., the sensor circuit and radiation source and receiver, may be designed analogously, as described using the above exemplary embodiments.

The measurement probe has a probe housing 302 that forms an indicator chamber 307 in the immersion region 301. A portion of the wall bounding the indicator chamber 307 is formed as a membrane 312 made of a porous ceramic. The indicator accommodated in the indicator chamber 307 contains species of an AIE-active substance that forms aggregates in the presence of an analyte, which aggregates show a higher fluorescence intensity than the unaggregated species of the AIE-active substance that are dissolved in the indicator. The indicator may contain as an additive an auxiliary substance that serves to keep the species of the AIE-active substance in solution via complexing or micelle formation. The indicator solution may be thickened by the auxiliary substance. The pores of the ceramic forming the membrane 312 are dimensioned so that the AIE-species and the auxiliary substance or the complexes or micelles formed do not pass through the membrane 312 into the measuring fluid. By contrast, measuring fluid with analyte may enter through the pores into the indicator chamber 307, such that the analyte concentration in the measuring medium influences the formation of fluorescing aggregates with participation of the species of the AIE-active substance in the manner described further above. In the manner already described, excitation radiation is radiated via the optical waveguide 315 into the indicator chamber 307, and, via the optical waveguide 315, fluorescence radiation is directed from the indicator chamber 307 back again to a radiation receiver (not shown) arranged in the measurement probe. A measurement value of the analyte concentration may be determined using the fluorescence radiation.

The membrane 312 may optionally have an analyte-sensitive coating on the inside, i.e., an analyte-sensitive coating arranged on the side of the membrane facing towards the indicator chamber 307. The diffusion paths are thereby reduced to a minimum, and the measurement value change takes place with a response time on the order of seconds instead of, as with conventional optochemical sensors of the prior art, on the order of minutes.

Figure 5:
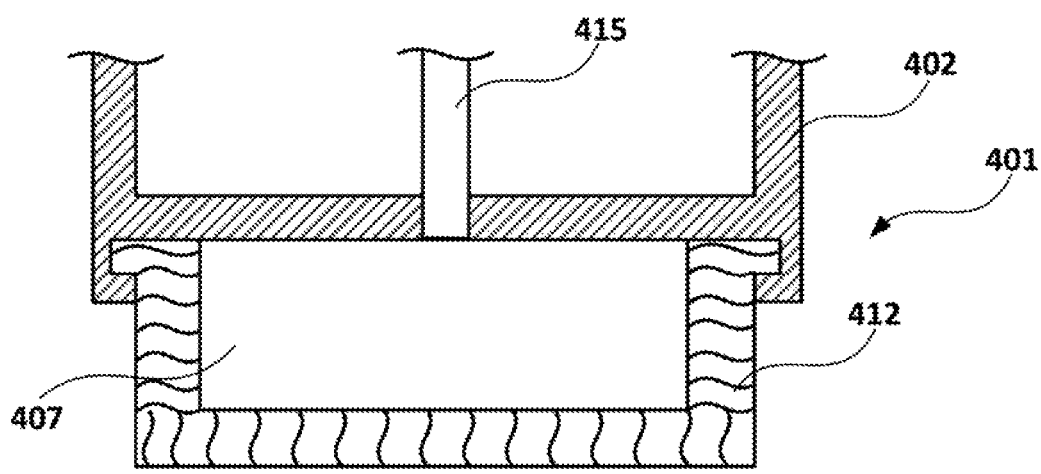
FIG. 5 shows a measurement probe in longitudinal section presentation, according to a fifth exemplary embodiment.

Schematically depicted in longitudinal section in FIG. 5 is the immersion region 401, designated for immersion into a measuring fluid, of a measurement probe according to a further exemplary embodiment. The immersion region 401 may be either a segment, facing the measuring fluid, of a sensor capsule which can be connected to a probe base body, similarly to the exemplary embodiment described using FIG. 3, or a forward end region of a measurement probe, similar to the measurement probe without detachable sensor capsule depicted in FIG. 1. The optical and electronic components of the measurement probe, i.e., the sensor circuit and radiation source and receiver, may be designed analogously, as described using the above exemplary embodiments.

The probe housing 402 of the measurement probe, together with a pot-shaped membrane body 412, forms an indicator chamber 407 in the immersion region 401. The membrane body 412 is comprised of a porous ceramic through whose pores an analyte may pass from the measuring fluid into the indicator chamber 407. Contained in the indicator chamber 407 is an advantageously higher-molecular indicator that comprises species of an AIE-active substance and other components of the indicator. The pore size of the pores in the membrane body 412 is adapted so that the species of the AIE-active substance cannot escape through the pores into the measuring fluid. The pot shape of the membrane body 412 allows a penetration over a large area of the analyte from multiple sides into the indicator chamber 407, and thus enables a further increase in the response time of the sensor in comparison to the example depicted in FIG. 4.

Influenced by the analyte penetrating into the indicator chamber, the species of the AIE-active substance contained in the indicator chamber form luminescent aggregates. To determine measurement values of the analyte concentration, excitation radiation may be radiated via the optical waveguides 415 into the indicator in the manner already described above, and luminescence radiation may be conducted via the optical waveguides 415 to the radiation receiver. A measurement value of the analyte concentration may be determined using the receiver signals.

A few examples of the concentration determination of various analytes using AIE-active substances are indicated in the following. The indicated reactions may be performed in measurement probes such as of those exemplary embodiments of the present disclosure, to determine measurement values of the analyte concentration by means of a luminescence measurement via the sensor circuit or by means of a data processing unit connected to this.

Example 1. Determination of a Concentration or Density of Living Cells in a Measuring Fluid A sensor according to one of the embodiments described in the preceding may be used for this, wherein, serving as a membrane, is a porous ceramic membrane that has pores whose diameter is dimensioned so that the cells may pass from the measuring fluid into the indicator chamber through the membrane. The quantity of cells contained in the indicator chamber is a measure of the concentration or density of living cells in the measuring fluid. The indicator contained in the indicator chamber may contain an AIE-active substance in the form of fluorescent nanoparticles (FNP's) or AIE dots. Suitable FNP's are described in, for example, X. Zhang et al., Aggregation induced emission-based fluorescent nanoparticles: fabrication methodologies and biomedical applications, J. Mater. Chem. B, 2014, 2, pages 4,398-4,414.

Suitable AIE dots are produced in the following manner, for example 4,7-bis[4-1,2,2-triphenylvinyl)phenyl]benzop-2,3,3-thadiazole (0.1 mg), 1,2-di stearoyl-sn-glycero-3-phosphoethanolamine-N-[methoxyl-polyethylene glycol)-2000] (0.1 mg), and 1,2-distearoyl-sn-glycero-3-phosphoethanolamine-N-[maleimide-polyethylene glycol)-2000] (0.1 mg) are dissolved in 1 mL tetrahydrofuran and added by drops into 10 mL water, wherein the mixture is simultaneously exposed to ultrasound with a microtip ultrasound device. The mixture is agitated at 500 rpm until all tetrahydrofuran has disappeared.

The AIE dots pass through the membrane of the cells located in the indicator chamber into said cells, and there form intensively luminescent aggregates whose luminescence efficiency is distinctly greater than that of the unaggregated AIE dots, for example, of dead cells. The concentration of the aggregates formed in the cells, and, derived from this, the concentration of the living cells that have passed into the indicator chamber, can thus be determined using luminescence measurements.

Example 2. Measurement of the pH Value of a Measuring Fluid

In the present example, an inline sensor with an immersion region provided for immersion into the measuring fluid, according to the embodiment described using FIG. 5, may be used to measure the pH value of said measuring fluid. Contained as an indicator in the indicator chamber is TPE-MAX, i.e., TPE (tetraphenylethylene) with a connected peptide chain of the sequence NH2-KRKRGSVKVKVKVKVDPPTVKVKVKVK-Am. This AIE-active substance is described in C. Zhang et al., A smart pH-switchable luminescent hydrogel, Chem. Comm., January 2015. The substance shows no luminescence or only slight luminescence at low pH values. At higher pH values, the species of the AIE-active substance organize into a luminescent hydrogel. The pH value of the measuring fluid can be determined using the luminescence radiation received by means of the radiation receiver.

Example 3. Measurement of a Glucose Concentration in a Measuring Fluid

The measurement of a glucose concentration in a measuring fluid may take place using an inline sensor according to one of the exemplary embodiments described further above, for example, of the exemplary embodiments described using FIGS. 1 and 2. Contained in the indicator chamber of the sensor, which is separated from the measuring fluid by a membrane permeable to glucose molecules, is an indicator solution that comprises as an AIE-active substance a bis(boronic acid)-functionalized TPE derivative, viz., TPEDB (1,2-diphenylethene-1,2-diyl)bis(1,4-phenylene)-1,1'diboronic acid). The glucose determination using this substance in a laboratory method is known from U.S. Pat. No. 9,051,598 B2. In the present example, instead of being dissolved in DMSO as in the laboratory method described in U.S. Pat. No. 9,051,598 B2, the AIE-active substance is dissolved in a higher-molecular compound, e.g., with units of dimethylsulfoxide, methylvinyl sulfone, allylmethyl sulfone, ethylvinyl sulfone or polyethylene sulfone, or combinations of these, so that the solvent cannot escape through the membrane into the measuring fluid.

With glucose molecules penetrating through the membrane into the indicator chamber, TPEDB molecules form fluorescent complex compounds. A glucose concentration of the measuring fluid may thus be determined using fluorescence measurements.

Example 4. Measurement of a Copper Ion Concentration in a Measuring Fluid

Ion concentrations in a measuring fluid may also be determined with a sensor according to one of the embodiments described in the preceding. For example, such a sensor for the measurement of a concentration of copper ions in a measuring fluid contains in its indicator chamber an indicator solution which contains, as an AIE active substance, TPIE modified with azide groups, as well as diethylene glycol-dipropionate. The indicator chamber is separated from the measuring fluid by a membrane permeable to Cu2+ ions. In the presence of Cu2+ ions, fluorescing aggregates form under participation of the TPE, modified with azide groups, with diethylene glycol-dipropionate. This reaction is described in J. Huang et al., Adaptive soft molecular self-assemblies, Soft Matter, 2016, 12, 337. The concentration of the Cu2+ ions in the measuring fluid can thus be determined by means of fluorescence measurements.

A plurality of additional detection reactions, known from the laboratory field, for the most varied analytes may, according to one of the embodiments described here, be used in the sensor according to the invention. New, long-lasting, and process-suited inline sensors are, in this way, achieved that may serve for monitoring and regulation of technical or industrial processes, such as automated processes.

The invention claimed is:

1. An optical measurement probe for detecting measurement values of a measurand of a measuring fluid, comprising:
    a probe housing having at least one immersion region configured to be immersed in the measuring fluid;
    an indicator chamber defined in the probe housing and closed on a side thereof in the immersion region of the probe housing by a membrane, wherein an indicator is contained in the indicator chamber, wherein the indicator comprises an aggregation-induced emission active (AIE-active) substance dissolved in a primary solvent to form an indicator solution or indicator gel, which AIE-active substance is formed from species whose luminescence efficiency is increased via formation of aggregates containing the species, wherein the primary solvent is water or an ionic liquid,
    wherein the indicator includes at least one auxiliary substance that increases the solubility of the AIE-active substance and/or decreases a boiling temperature of the indicator, wherein the at least one auxiliary substance is different than the primary solvent and is a compound having a molecular weight of greater than 200 g/mol;
    a radiation source disposed in the probe housing and configured to emit radiation into the indicator chamber as to generate radiation in the indicator; and
    a radiation receiver disposed in the probe housing and configured to detect the generated radiation emitted from the indicator within the chamber,
    wherein the measurand represents a concentration of an analyte in the measuring medium determined from the generated radiation emitted from the indicator, which is detected by the radiation receiver,
    wherein the membrane is permeable to the analyte, and wherein the membrane is impermeable to the AIE-active substance of the indicator and to the at least one auxiliary substance.

2. The optical measurement probe of claim 1, wherein the indicator chamber is disposed in a sensor capsule connected to a probe body, wherein the probe housing comprises the sensor capsule and the probe body.

3. The optical measurement probe of claim 2, wherein the sensor capsule is reversibly connected to the probe body.

4. The optical measurement probe of claim 2, further comprising a sensor circuit electrically connected to the radiation source and the radiation receiver, wherein the radiation source, the radiation receiver and the sensor circuit are disposed in the probe body.

5. The optical measurement probe of claim 1, further comprising an optical waveguide adapted to guide radiation emitted from the radiation source into the indicator chamber and to guide luminescence radiation from the indicator chamber to the radiation receiver.

6. The optical measurement probe of claim 1, wherein the indicator chamber is fluidically connected via a first fluid conduit to a reservoir disposed outside of the indicator chamber, the reservoir containing a liquid including the indicator.

7. The optical measurement probe of claim 6, wherein the indicator chamber is fluidically connected to a second fluid conduit for liquid discharge from the indicator chamber.

8. The optical measurement probe of claim 2, further comprising an ultrasound source integrated into the sensor capsule and configured to agitate the indicator as to facilitate homogenization of the indicator in the indicator chamber.

9. The optical measurement probe of claim 1, wherein the at least one auxiliary substance is a surfactant, or wherein the AIE-active substance is a surfactant, having a polar part and a non-polar part, which may form micelles in solution.

10. The optical measurement probe of claim 1, wherein the indicator includes an inorganic or organic pH buffer.

11. The optical measurement probe of claim 1, wherein the indicator is composed as to be temperature-stable up to a temperature of at least 120° C. and/or remains stable upon irradiation with gamma radiation of more than 5 kGy.

12. The optical measurement probe of claim 11, wherein the indicator is further composed to remain stable upon irradiation with gamma radiation of more than 25 kGy.

13. An arrangement for detecting measurement values of a measurand of a measuring fluid, the arrangement comprising:
    an optical measurement probe including:
        a probe housing having at least one immersion region configured to be immersed in the measuring fluid;
        an indicator chamber defined in the probe housing and closed on a side thereof in the immersion region of the probe housing by a membrane, wherein an indicator is contained in the indicator chamber, wherein the indicator comprises an aggregation-induced emission active (AIE-active) substance dissolved in a primary solvent to form an indicator solution or indicator gel, which AIE-active substance is formed from species whose luminescence efficiency is increased via formation of aggregates containing the species, wherein the primary solvent is water or an ionic liquid
        wherein the indicator includes at least one auxiliary substance that increases the solubility of the AIE-active substance and/or decreases a boiling temperature of the indicator, wherein the at least one auxiliary substance is different than the primary solvent and is a compound having a molecular weight of greater than 200 g/mol;
        a radiation source disposed in the probe housing and configured to emit radiation into the indicator chamber as to generate radiation in the indicator; and
        a radiation receiver disposed in the probe housing and configured to detect the generated radiation emitted from the indicator within the chamber,
        wherein the measurand represents a concentration of an analyte in the measuring medium determined from the generated radiation emitted from the indicator, which is detected by the radiation receiver, wherein the membrane is permeable to the analyte, and wherein the membrane is impermeable to the AIE-active substance of the indicator and to the at least one auxiliary substance; and a superordinate unit in communication with the measurement probe, wherein the measurement probe and the superordinate unit are coupled with one another via a releasable connection, the connection configured to transmit energy uni-directionally from the superordinate unit to the measurement probe.

14. The arrangement of claim 13, wherein the superordinate unit is a measuring transducer, control electronics or power supply, and wherein the connection is an inductive coupling or a radio connection.

15. The arrangement of claim 13, wherein the connection is a galvanically-isolated connection.

16. The arrangement of claim 13, wherein the superordinate unit includes a data processing unit, and wherein data are transmitted bi-directionally between the measurement probe and the superordinate data processing unit via the connection.

17. The optical measurement probe of claim 1, wherein the indicator chamber includes a coating on surfaces of the indicator chamber in contact with the indicator contained in the indicator chamber, the coating configured to counteract an aggregation of the AIE-active substance at an interface between the indicator chamber and the indicator.

18. An optical measurement probe for detecting measurement values of a measurand of a measuring fluid, comprising:
a probe housing having at least one immersion region configured to be immersed in the measuring fluid;
an indicator chamber defined in the probe housing and closed on a side thereof in the immersion region of the probe housing by a membrane, wherein an indicator is contained in the indicator chamber, wherein the indicator comprises an aggregation-induced emission active (AIE-active) substance dissolved in a primary solvent to form an indicator solution or indicator gel, which AIE-active substance is formed from species whose luminescence efficiency is increased via formation of aggregates containing the species, wherein the primary solvent is water or an ionic liquid,
wherein the indicator includes at least one auxiliary substance that increases the solubility of the AIE-active substance and/or decreases a boiling temperature of the indicator, wherein the at least one auxiliary substance is different than the primary solvent and is a compound having a molecular weight of greater than 200 g/mol;
a radiation source disposed in the probe housing and configured to emit radiation into the indicator chamber as to generate radiation in the indicator; and
a radiation receiver disposed in the probe housing and configured detect the generated radiation emitted from the indicator within the chamber,
wherein the measurand represents a concentration of an analyte in the measuring medium determined from the generated radiation emitted from the indicator, which is detected by the radiation receiver,
wherein the membrane is permeable to the analyte, and wherein the membrane is impermeable to the AIE-active substance of the indicator and to the at least one auxiliary substance,
wherein materials comprising the membrane and/or the indicator chamber are functionalized with functional groups that suppress aggregation of the A1E-active substance at an interface between the membrane and the indicator contained in the indicator chamber and/or between the indicator chamber and the indicator.

19. The optical measurement probe of claim 1, wherein the membrane includes a coating on a side of the membrane adjacent the indicator chamber, the coating configured to counteract an aggregation of the AIE-active substance at an interface between the membrane and the indicator contained in the indicator chamber.

20. The arrangement of claim 13, wherein the membrane includes a coating on a side of the membrane adjacent the indicator chamber, the coating configured to counteract an aggregation of the AIE-active substance at an interface between the membrane and the indicator contained in the indicator chamber.

21. The arrangement of claim 13, wherein the indicator chamber includes a coating on surfaces of the indicator chamber in contact with the indicator contained in the indicator chamber, the coating configured to counteract an aggregation of the AIE-active substance at an interface between the indicator chamber and the indicator.

22. The optical measurement probe of claim 1, wherein the at least one auxiliary substance includes at least one of oligomers, polymers or dendrimers with units of dimethyl sulfoxide, methylvinyl sulfone, allylmethyl sulfone, ethylvinyl sulfone and polyethylene sulfone.

* * * * *